(12) United States Patent
Bedard et al.

(10) Patent No.: US 10,821,427 B2
(45) Date of Patent: Nov. 3, 2020

(54) PROCESSES FOR REGENERATING CATALYSTS

(71) Applicant: ExxonMobil Chemical Patents Inc., Baytown, TX (US)

(72) Inventors: Jeremy W. Bedard, Humble, TX (US); Larry L. Iaccino, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 138 days.

(21) Appl. No.: 15/942,821

(22) Filed: Apr. 2, 2018

(65) Prior Publication Data

US 2018/0318812 A1 Nov. 8, 2018

Related U.S. Application Data

(60) Provisional application No. 62/500,795, filed on May 3, 2017.

(51) Int. Cl.
*B01J 29/90* (2006.01)
*C07C 5/387* (2006.01)
(Continued)

(52) U.S. Cl.
CPC .............. *B01J 29/90* (2013.01); *B01J 29/44* (2013.01); *B01J 29/46* (2013.01); *B01J 38/44* (2013.01);
(Continued)

(58) Field of Classification Search
CPC ... B01J 29/90; B01J 29/44; B01J 29/46; B01J 29/40; B01J 31/40; B01J 31/4015;
(Continued)

(56) References Cited

U.S. PATENT DOCUMENTS 3,986,982 A * 10/1976 Crowson .................. B01J 29/90
502/37
4,013,546 A  3/1977 Suggitt et al.
(Continued)

FOREIGN PATENT DOCUMENTS

WO        91/13682 A    9/1991
WO     2011/056917      5/2011

OTHER PUBLICATIONS

Foger, K. et al., "Redispersion of Pt-zeolite Catalysts with Chlorine," Applied Catalysis, Vvol. 56, pp. 137-147, 1989.
(Continued)

*Primary Examiner* — Patricia L. Hailey

(57) ABSTRACT

Disclosed are processes for regenerating catalysts comprising at least one Group 10 metal and a microporous crystalline aluminosilicate having a having a molar ratio of Group 10 metal to Al of greater than or equal to about 0.007:1, and hydrocarbon conversion processes including such regeneration processes. In an aspect, the regeneration processes comprise an oxychlorination step comprising contacting the catalyst with a first gaseous stream comprising a chlorine source and an oxygen source under conditions effective for dispersing at least a portion of the at least one Group 10 metal on the surface of the catalyst and for producing a first Group 10 metal chlorohydrate. The processes further comprise a chlorine stripping step comprising contacting the catalyst with a second gaseous stream comprising an oxygen source, and optionally a chlorine source, under conditions effective for increasing the O/Cl ratio of the first Group 10 metal chlorohydrate to produce a second Group 10 metal chlorohydrate.

22 Claims, 3 Drawing Sheets

(51) Int. Cl.
  *B01J 29/44* (2006.01)
  *B01J 38/44* (2006.01)
  *B01J 29/46* (2006.01)
  *C07C 5/333* (2006.01)
  *C07C 5/373* (2006.01)

(52) U.S. Cl.
  CPC .............. *C07C 5/333* (2013.01); *C07C 5/373* (2013.01); *C07C 5/387* (2013.01); *C07C 2529/44* (2013.01); *C07C 2529/46* (2013.01); *C07C 2601/08* (2017.05); *C07C 2601/10* (2017.05)

(58) Field of Classification Search
  CPC ........ B01J 31/4092; B01J 38/02; B01J 38/04; B01J 38/10; B01J 38/14; B01J 38/42; B01J 38/44
  USPC ................................. 502/34, 35, 38
  See application file for complete search history.

(56) References Cited

U.S. PATENT DOCUMENTS

| | | | |
|---|---|---|---|
| 4,218,338 A * | 8/1980 | Huin | ............................ B01J 8/12 502/37 |
| 4,657,874 A | 4/1987 | Borghard et al. | |
| 4,855,269 A * | 8/1989 | Mohr | ....................... B01J 29/90 502/37 |
| 5,155,074 A | 10/1992 | Mohr | |
| 5,776,849 A | 7/1998 | Fung et al. | |
| 5,866,495 A | 2/1999 | Fung et al. | |
| 7,045,477 B2 * | 5/2006 | Zhao | ........................ B01J 8/125 502/35 |
| 9,849,440 B2 | 12/2017 | Iaccino et al. | |
| 2008/0154079 A1 | 6/2008 | Ellis et al. | |
| 2012/0083637 A1 | 4/2012 | Clem et al. | |
| 2012/0277089 A1 | 11/2012 | Iyer et al. | |
| 2017/0121245 A1 | 5/2017 | Iaccino et al. | |
| 2017/0121246 A1 | 5/2017 | Iaccino et al. | |
| 2017/0121253 A1 | 5/2017 | Iaccino et al. | |
| 2017/0121254 A1 | 5/2017 | Iaccino et al. | |
| 2018/0318813 A1 * | 11/2018 | Iaccino | .................... B01J 29/90 |

OTHER PUBLICATIONS

Foger, K. et al., "The Effect of Chlorine Treatment on the Dispersion of Platinum Metal Particles Supported on Silica and γ-Alumina," Journal of Catalysis, vol. 92, pp. 64-78, 1985.

Fung, S.C., "Deactivation and Regeneration/Redispersion Chemistry of Pt/KL-Zeolite," Studies in Surface Science and Catalysis, vol. 139, pp. 399-406, 2001.

Anderson, J. A., et al., "Infrared Study of the Effects of Oxidation/Reduction Treatments on Pt Dispersion in Pt/Al2O3 Catalysts," Journal of the Chemical Society, vol. 85, Issue 9, pp. 2983-2990, 1989.

Galisteo, F. C., et al., "Reactivation of sintered Pt/Al2O3 oxidation catalysts," Applied Catalysis B: Environmental, vol. 59, pp. 227-233, 2005.

* cited by examiner

PROCESSES FOR REGENERATING CATALYSTS

CROSS-REFERENCE TO RELATED APPLICATION

This application claims priority to U.S. Provisional Application Ser. No. 62/500,795, filed May 3, 2017, the disclosures of which is incorporated herein by reference.

FIELD OF THE INVENTION

The present invention relates to processes for regenerating catalysts comprising a Group 10 metal and a microporous crystalline aluminosilicate.

BACKGROUND OF THE INVENTION

Supported noble metal, e.g., platinum containing catalysts are widely utilized in hydrocarbon conversion processes. Such catalysts generally lose activity over time, in large part due to the formation of coke. When the activity of the catalyst is reduced to an unsatisfactory level, the catalyst must be discarded or more preferably, reconditioned or regenerated so that it can be reused.

Conventional catalyst regeneration methods typically comprise burning coke off the catalyst under oxidation conditions sufficient to remove substantially all of the coke from the catalyst. However, these conventional oxidative coke removal methods generally result in agglomeration of the supported metal particles.

Numerous methods have been described for the redispersion of agglomerated noble metal particles on alumina, silica, and zeolite supports. Some references of potential interest in this regard may include: U.S. Pat. Nos. 3,986,982; 4,657,874; 5,866,495; U.S. Patent Pub. No. 2012/0277089; and the following publications: (1) K. Foger and H. Jaeger, "Redispersion of Pt-Zeolite Catalysts with Chlorine," *Journal of Catalysis*, Vol. 56, pp. 137-147, 1989; (2) K. Foger and H. Jaeger, "The Effect of Chlorine Treatment on the Dispersion of Platinum Metal Particles Supported on Silica and γ-Alumina," *Journal of Catalysis*, Vol. 92, pp. 64-78, 1985; (3) S. C. Fung, "Deactivation and Regeneration/Redispersion Chemistry of Pt/KL-Zeolite," in J. J. Spivey, G. W. Roberts, and B. H. Davis (Eds.), *Studies in Surface Science and Catalysis*, Vol. 249, pp. 399-406, 2001; (4) J. A. Anderson, M. G. V. Mordente, and C. H. Rochester, "Infrared Study of the Effects of Oxidation/Reduction Treatments on Pt Dispersion in $Pt/Al_2O_3$ Catalysts," *Journal of the Chemical Society, Faraday Transactions* 1: *Physical Chemistry in Condensed Phases*, Vol. 85, pp. 2983-2990, 1989; and (5) F. C. Galisteo, R. Mariscal, M. L. Granados, J. L. G. Fierro, R. A. Daley, and J. A. Anderson, "Reactivation of Sintered $Pt/Al_2O_3$ Oxidation Catalysts," *Applied Catalysis B: Environmental*, Vol. 59, pp. 227-233, 2005.

The redispersion of agglomerated noble metal particles on zeolite supported catalysts is particularly challenging because the metal must be returned in a dispersed form within the zeolite pores. Current methods of redispersing noble metal particles in Group 10 metal-containing zeolites are limited to materials where the Group 10 metal-to-aluminum molar ratio is less than 0.007:1. There remains a need, therefore, for methods of catalyst regeneration suitable for higher Group 10 metal-to-aluminum ratio materials.

SUMMARY OF THE INVENTION

The present invention relates to processes for regenerating catalysts comprising a Group 10 metal and a microporous crystalline aluminosilicate that address the need for methods of regenerating high Group 10 metal-to-aluminum ratio materials.

In a first aspect, the invention relates to processes for regenerating a deactivated catalyst comprising at least one Group 10 metal and a microporous crystalline aluminosilicate having a molar ratio of Group 10 metal to Al of greater than or equal to about 0.007:1. The processes comprise an oxychlorination step comprising contacting the catalyst with a first gaseous stream comprising a chlorine source and an oxygen source under conditions effective for dispersing at least a portion of the at least one Group 10 metal on the surface of the catalyst and for producing a first Group 10 metal chlorohydrate. The processes further comprise a chlorine stripping step comprising contacting the catalyst with a second gaseous stream comprising an oxygen source, and optionally a chlorine source, under conditions effective for increasing the O/Cl ratio of the first Group 10 metal chlorohydrate to produce a second Group 10 metal chlorohydrate.

The invention further relates to processes for the chemical conversion of a hydrocarbon feedstock. Such processes comprise the step of contacting a hydrocarbon feedstock with a catalyst comprising at least one Group 10 metal and a microporous crystalline aluminosilicate having a molar ratio of Group 10 metal to Al of greater than or equal to about 0.007:1 in a reaction zone to form a hydrocarbon reaction product. The processes further comprise the steps of forming deactivated catalyst from the catalyst and regenerating the deactivated catalyst in accordance with the regeneration processes of this invention.

DETAILED DESCRIPTION OF THE PREFERRED EMBODIMENTS

Figure 1:
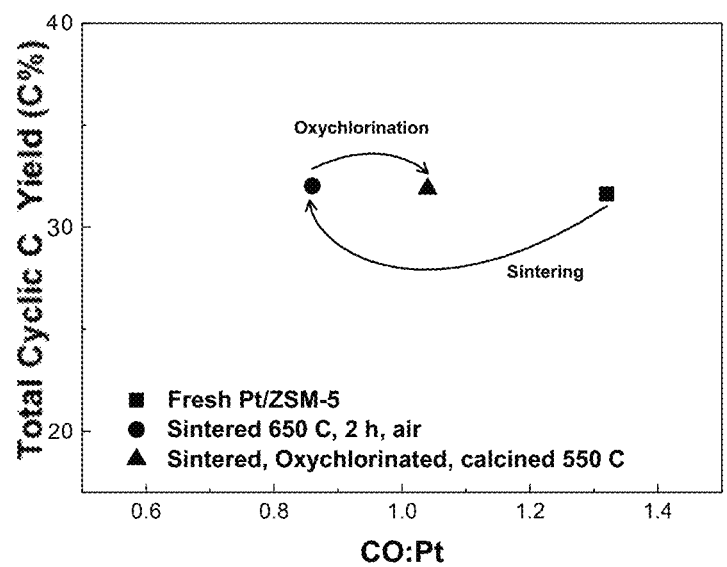
FIG. 1 shows the yield of cyclic $C_5$ as a function of CO to Pt uptake values resulting from the performance evaluation of fresh, sintered, and regenerated catalyst compositions conducted in Example 3.

Disclosed herein are processes useful in regenerating Group 10 metal-containing zeolite catalysts which have become deactivated during a hydrocarbon conversion processing step. The present methods are particularly suitable in hydrocarbon conversion processes comprising the conversion of acyclic hydrocarbons to alkenes, cyclics, and/or aromatics.

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

Definitions

For the purpose of this specification and appended claims, the following terms are defined.

The term "hydrocarbon" means a class of compounds containing hydrogen bound to carbon, and encompasses (i)

saturated hydrocarbon compounds, (ii) unsaturated hydrocarbon compounds, and (iii) mixtures of hydrocarbon compounds (saturated and/or unsaturated), including mixtures of hydrocarbon compounds having different values of n. The term "$C_n$" means hydrocarbon(s) having n carbon atom(s) per molecule, wherein n is a positive integer.

As used herein, the term "light hydrocarbon" means light paraffinic and/or olefinic hydrocarbons comprised substantially of hydrogen and carbon only and has one to no more than 4 carbon atoms.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclic hydrocarbon" denotes groups such as the cyclopropane, cyclopropene, cyclobutane, cyclobutadiene, etc., and substituted analogues of these structures. These cyclic hydrocarbons can be single- or multi-ring structures. Preferably, the term "cyclic hydrocarbon" refers to non-aromatics.

The term "cyclic $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene (CPD) spontaneously dimerizes over time to form dicyclopentadiene (DCPD) via Diels-Alder condensation over a range of conditions, including ambient temperature and pressure.

The term "acyclics" includes, but is not limited to, linear and branched saturates and non-saturates.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "alkene," alternatively referred to as "olefin," refers to a branched or unbranched unsaturated hydrocarbon having one or more carbon-carbon double bonds. A simple alkene comprises the general formula $C_nH_{2n}$, where n is 2 or greater. Examples of alkenes include, but are not limited to ethylene, propylene, butylene, pentene, hexene and heptene. "Alkene" is intended to embrace all structural isomeric forms of an alkene. For example, butylene encompasses but-1-ene, (Z)-but-2-ene, etc.

The term "aromatic" means a planar cyclic hydrocarbyl with conjugated double bonds, such as, for example, benzene. As used herein, the term aromatic encompasses compounds containing one or more aromatic rings, including, but not limited to, benzene, toluene, and xylene, and polynuclear aromatics (PNAs), which include, but are not limited to, naphthalene, anthracene, chrysene, and their alkylated versions. The term "$C_{6+}$ aromatics" includes compounds based upon an aromatic ring having six or more ring atoms, including, but not limited to, benzene, toluene, and xylene and polynuclear aromatics (PNAs) which include, but are not limited to, naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_{n+}$" means hydrocarbon(s) having at least n carbon atom(s) per molecule.

The term "$C_{n-}$" means hydrocarbon(s) having no more than n carbon atom(s) per molecule.

The term "$C_5$ feedstock" includes a feedstock containing n-pentane, such as, for example, a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, nickel, palladium, platinum, and a mixture of two or more thereof.

The term "Group 11 metal" means an element in Group 11 of the Periodic Table and includes, but is not limited to, copper, silver, gold, and a mixture of two or more thereof.

The term "Group 1 alkali metal" means an element in Group 1 of the Periodic Table and includes, but is not limited to, lithium, sodium, potassium, rubidium, cesium, and a mixture of two or more thereof, and excludes hydrogen.

The term "Group 2 alkaline earth metal" means an element in Group 2 of the Periodic Table and includes, but is not limited to, beryllium, magnesium, calcium, strontium, barium, and a mixture of two or more thereof.

The term "rare earth metal" means an element in the Lanthanide series of the Periodic Table, as well as scandium and yttrium. The term rare earth metal includes, but is not limited to, lanthanum, praseodymium, neodymium, cerium, yttrium, and a mixture of two or more thereof.

The term "constraint index" is defined in U.S. Pat. Nos. 3,972,832 and 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology (A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "zeolite" or "microporous crystalline material."

As used herein, the term "selectivity" means the moles of carbon in the respective cyclic $C_5$, CPD, $C_1$, and $C_{2-4}$ formed divided by total moles of carbon in the pentane converted. For example, the term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The term "conversion of at least 70% of said acyclic $C_5$ feedstock to a product" means that at least 70% of the moles of said acyclic $C_5$ feedstock was converted to a product.

As used herein, the term "Alpha Value" is used as a measure of the cracking activity of a catalyst and is described in U.S. Pat. No. 3,354,078 and in the Journal of Catalysis, Vol. 4, p. 527 (1965); Vol. 6, p. 278, (1966); and Vol. 61, p. 395, (1980), each incorporated herein by reference. The experimental conditions of the test used herein included a constant temperature of 538° C. and a variable flow rate as described in detail in the Journal of Catalysis, Vol. 61, p. 395, (1980).

As used herein, "deactivated catalyst" refers to catalyst that has lost activity during the course of a hydrocarbon conversion process, e.g., due to the accumulation of coke and/or agglomeration of metal.

As used herein, "regenerated catalyst" and "rejuvenated catalyst" refer to deactivated catalyst that has been treated to restore at least a portion of the lost activity. Regenerated catalyst is catalyst that has been treated in the presence of chlorine.

As used herein, the term "reactor system" refers to a system including one or more reactors and all optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein, the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes, including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and tr is transport velocity. These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$, in at least a portion of the reaction zone, and/or operating at a velocity higher than the minimum fluidization velocity, while maintaining a gradient in gas and/or solid property (such as, temperature, gas, or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%.

As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor, such as a circulating fluidized bed reactor, may be operated as a riser reactor.

As used herein, the term "radiantly heated tubular" or "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "fixed bed" or "packed bed" reactor refers to a zone or vessel (such as, vertical or horizontal, cylindrical pipe or a spherical vessel) and may include transverse (also known as cross flow), axial flow, and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval, and/or a regeneration interval. The duration and/or order of the interval steps may change over time.

As used herein, the term "co-current" refers to a flow of two streams (stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Catalyst Composition

Catalyst compositions useful herein comprise a microporous crystalline aluminosilicate and a Group 10 metal. Suitable catalyst compositions are further characterized by having a Group 10 metal content-to-Al content molar ratio of greater than or equal to about 0.007:1, such as greater than or equal to about 0.01:1, or greater than or equal to about 0.05:1, or greater than or equal to about 0.1:1. For example, suitable catalysts compositions may have a Group 10 metal content-to-Al content molar ratio ranging from about 0.007:1 to about 0.1:1, or from about 0.01:1 to about 0.5:1.

It should be recognized for purposes of the invention that an aluminosilicate may have one or more metals present apart from aluminum. For example, in addition to aluminum, an aluminosilicate may contain one or more metals from groups 8, 11, 13, and 14 of the Periodic Table of the Elements (preferably one or more of Fe, Cu, Ag, Au, B, Al, Ga, and or In) that are incorporated in the crystal structure during synthesis or impregnated post crystallization.

The microporous crystalline aluminosilicate has a constraint index in the range of about 3 to about 12. Suitable aluminosilicates having a constraint index of about 3 to about 12 include and are selected from the group consisting of ZSM-5, ZSM-11, ZSM-22, ZSM-23, ZSM-35, ZSM-48, ZSM-50, ZSM-57, ZSM-58, a MCM-22 family material and mixtures of two or more thereof. Preferably, the microporous crystalline aluminosilicate that has a constraint index in the range of about 3 to about 12 is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures of two or more thereof. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), and ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

The microporous crystalline aluminosilicate has a $SiO_2/Al_2O_3$ molar ratio greater than about 25, or greater than about 50, or greater than about 100, or greater than about 400, or greater than about 1,000, or in the range from about 100 to about 400, or from about 100 to about 500, or from about 50 to 1000.

The Group 10 metal includes, or is selected from the group consisting of nickel, palladium, and platinum, preferably platinum. The Group 10 metal content of said catalyst composition is at least 0.005 wt %, based on the weight of the catalyst composition. The Group 10 content is in the range from about 0.005 wt % to about 10 wt %, or from about 0.005 wt % up to about 1.5 wt %, based on the weight of the catalyst composition.

Optionally, the Group 10 metal is present in combination with an additional metal selected from Groups 8, 9, 11, and 13 of the Periodic Table of the Elements and the rare earth metals, such as Ga, In, Zn, Cu, Re, Mo, W, La, Fe, Ag, Rh, Pr, La, and/or oxides, sulfides, nitrides, and/or carbides of these metals. Alternatively, or additionally, the Group 10 metal is present in combination with a Group I alkali metal and/or a Group 2 alkaline earth metal.

Preferred additional metals are Group 11 metals. Typically, the Group 11 metal is selected from the group consisting of Cu, Ag, Au, and mixtures of two or more thereof; preferably Cu or Ag. The Group 11 metal content of the catalyst composition is such that the molar ratio of Group 11 metal to Group 10 metal is at least 0.01, based on the molar quantities of each in the catalyst composition. Preferably, the molar ratio of Group 11 metal to Group 10 metal is in the range from about 0.1 to 10 or from about 0.5 to 5 based on the molar quantities of each in the catalyst composition. The Group 11 metal may be added to the catalyst composition during or after synthesis of the microporous crystalline molecular sieve as any suitable Group 11 metal compound.

A preferred Group 9 metal is Rh, which may form an alloy with the Group 10 metal. Preferably, the molar ratio of Rh to Group 10 metal is in the range from about 0.1 to about 5.

Typically, the rare earth metal is selected from the group consisting of yttrium, lanthanum, cerium, praseodymium, and mixtures or combinations thereof. Preferably, the molar ratio of rare earth metal to Group 10 metal is in the range from about 1 to about 10. The rare earth metal may be added to the catalyst composition during or after synthesis of the microporous crystalline molecular sieve as any suitable rare earth metal compound.

The catalyst composition has an Alpha Value (as measured prior to the addition of the Group 10 metal, preferably platinum, and/or prior to the addition of the optional Group 8-13 metal, preferably, copper or silver) is less than about 25, or in the range of greater than about 1 to less than about 25, preferably, less than about 15, or in the range of greater than about 1 to less than about 15.

The Group 1 alkali metal is generally present as an oxide and the metal is selected from the group consisting of lithium, sodium, potassium, rubidium, cesium, and mixtures of two or more thereof. The Group 2 alkaline earth metal is generally present as an oxide and the metal is selected from the group consisting of beryllium, magnesium, calcium, strontium, barium, and mixtures of two or more thereof.

The molar ratio of said Group 1 alkali metal to Al is at least about 0.5, or at least about 1, or in the from at least about 1 up to about 3, preferably at least about 2, more preferably at least about 3. The molar ratio of said Group 2 alkaline earth metal to Al is at least about 0.5, or at least about 1, or from at least about 1 up to about 3, preferably at least about 2, more preferably at least about 3.

The catalyst compositions of this invention can be combined with a matrix or binder material to render them attrition resistant and more resistant to the severity of the conditions to which they will be exposed during use in hydrocarbon conversion applications. Preferred binder materials comprise one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof. Preferably, suitable binder materials have a lower affinity for Group 10 metal particles, e.g., Pt, in comparison with the crystalline metallosilicate, e.g., aluminosilicate. The combined compositions can contain 1 wt % to 99 wt % of the materials of the invention based on the combined weight of the matrix (binder) and material of the invention. The relative proportions of microporous crystalline material and matrix may vary widely, with the crystal content ranging from about 1 wt % to about 90 wt % and more usually, particularly when the composite is prepared in the form of beads, in the range of about 2 wt % to about 80 wt % of the composite.

The formulated catalyst composition may be made into one or more forms. For example, the formulated catalyst can be extruded to form an extrudate, particularly into a shaped extrudate having a geometric form. Also, the formulated catalyst composition may be made into a particle, such as, for example, a spray dried particle, an oil drop particle, a mulled particle, or a spherical particle. The formulated catalyst composition may be made into a slurry.

The catalyst compositions can be made by the methods according to the Examples, below.

Feedstock

Feedstock useful herein generally comprises acyclic hydrocarbons, preferably acyclic $C_2$-$C_{10}$ hydrocarbons. Acyclic $C_2$-$C_{10}$ hydrocarbons include, but are not limited to alkanes (e.g., ethane, propane, butane, pentane, hexane, etc.), alkenes (e.g., ethylene, propylene, butylene, etc.), alkynes (e.g., ethyne, propyne, 1-butyne, 2-butyne, etc.), dialkenes (e.g., 1,2-propadiene, 1,3-butadiene, 1,3-pentadiene, etc.) and combinations thereof. An acyclic $C_2$-$C_{10}$ hydrocarbon feedstock, useful herein, is obtainable from crude oil or natural gas condensate.

In various aspects, the feedstock may preferably be an acyclic $C_5$ feedstock and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the process of this invention comprises pentane, pentene, pentadiene and mixtures of two or more thereof. Preferably, in one or more embodiments, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ hydrocarbon feedstock optionally does not comprise $C_6$ aromatic compounds, such as benzene. Preferably $C_6$ aromatic compounds are present at less than 5 wt %, preferably less than 1 wt %, preferably less than 0.01 wt %, and preferably at zero wt %. Additionally, or alternatively, the acyclic $C_5$ hydrocarbon feedstock optionally does not comprise benzene, toluene, or xylene (ortho, meta, or para). Preferably, any benzene, toluene, or xylene (ortho, meta, or para) compounds are present at less than 5 wt %, preferably less than 1 wt %, preferably less than 0.01 wt %, and preferably at zero wt %.

The acyclic $C_5$ hydrocarbon feedstock optionally does not comprise $C_{6+}$ aromatic compounds. Preferably, $C_{6+}$ aromatic compounds are present at less than 5 wt %, preferably less than 1 wt %, preferably less than 0.01 wt %, and preferably at zero wt %.

Hydrocarbon Conversion Processes

In any embodiment, the catalyst regeneration processes of this disclosure are generally employed in hydrocarbon conversion processes that comprise contacting a hydrocarbon feedstock with any one of the aforementioned catalyst compositions in at least one reaction zone to form a hydrocarbon reaction product. Examples of suitable hydrocarbon conversion processes include: the conversion of acyclic $C_5$ hydrocarbons to cyclic $C_5$ hydrocarbons; the conversion of acyclic $C_{6+}$ hydrocarbons to aromatic $C_{6+}$ hydrocarbons; the conversion of $C_2$-$C_5$ hydrocarbons to $C_{6+}$ aromatics; and/or the dehydrogenation of paraffins to olefins and/or dienes.

In any embodiment, suitable hydrocarbon conversion processes can be conducted in a wide range of reactor configurations. Particularly preferred reactor configurations include convectively heated tubes (as described in U.S. Ser. No. 62/250,674, filed Nov. 4, 2015); fired tubes (as described in U.S. Ser. No. 62/250,693, filed Nov. 4, 2015); a riser reactor (as described in U.S. Ser. No. 62/250,682, filed Nov. 4, 2015); a circulating fluidized bed or a circulating settling bed with counter-current flow (as described in U.S. Ser. No. 62/250,680, filed Nov. 4, 2015); a cyclic fluidized bed reactor or a cyclic fixed bed reactor (as described in U.S. Ser. No. 62/250,677, filed Nov. 4, 2015); and/or an electrically heated reactor. In addition, suitable hydrocarbon conversion processes can be conducted in a single reaction zone or in a plurality of reaction zones, such as an adiabatic reaction zone followed by a diabatic reaction zone (as described in U.S. Ser. No. 62/250,697, filed Nov. 4, 2015).

Acyclic $C_5$ Conversion Process

A particularly preferred hydrocarbon conversion process is the conversion of acyclic $C_5$ hydrocarbons to cyclic $C_5$ hydrocarbons, the process comprising the steps of contacting said feedstock and, optionally, hydrogen under acyclic $C_5$ conversion conditions in the presence of any one of the aforementioned catalyst compositions to form said product.

Typically, the acyclic $C_5$ hydrocarbon(s) contained in the $C_5$ feedstock is fed into a first reactor loaded with a catalyst, where the acyclic $C_5$ hydrocarbons contact the catalyst under conversion conditions, whereupon at least a portion of the acyclic $C_5$ hydrocarbon(s) molecules are converted into CPD molecules, and a reaction product containing CPD and, optionally, other cyclic hydrocarbons (e.g., $C_5$ cyclic hydrocarbons such as cyclopentane and cyclopentene) exits the first reactor as a first reactor hydrocarbon effluent. Preferably, a hydrogen co-feedstock comprising hydrogen and, optionally, light hydrocarbons, such as $C_1$-$C_4$ hydrocarbons, is also fed into the first reactor (as described in U.S. Ser. No. 62/250,702, filed Nov. 4, 2015). Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles.

The product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. The cyclic $C_5$ compounds comprise at least about 20 wt %, or 30 wt %, or 40 wt %, or 50 wt % cyclopentadiene, or in the range of from about 10 wt % to about 80 wt %, alternately 20 wt % to 70 wt % of cyclopentadiene.

The acyclic $C_5$ conversion conditions include at least a temperature, a partial pressure, and a weight hourly space velocity (WHSV). The temperature is in the range of about 400° C. to 700° C., or about 450° C. to about 800° C., or in the range from about 500° C. to about 650° C., preferably, in the range from about 500° C. to about 600° C.

The partial pressure is in the range of about 3 psia to about 100 psia at the reactor inlet (21 to 689 kPa-a), or in the range from about 3 psia to about 50 psia (21 to 345 kPa-a), preferably, in the range from about 3 psia to about 20 psia (21 to 138 kPa-a). The weight hourly space velocity is in the range from about 1 $hr^{-1}$ to about 50 $hr^{-1}$, or in the range from about 1 $hr^{-1}$ to about 20 $hr^{-1}$. Such conditions include a molar ratio of the optional hydrogen co-feed to the acyclic $C_5$ hydrocarbon in the range of about 0 to 3 (e.g., 0.01 to 3.0), or in the range from about 0.5 to about 2. Such conditions may also include co-feed $C_1$-$C_4$ hydrocarbons with the acyclic $C_5$ feed.

In any embodiment, this invention relates to a process for conversion of n-pentane to cyclopentadiene comprising the steps of contacting n-pentane and, optionally, hydrogen (if present, typically $H_2$ is present at a molar ratio of hydrogen to n-pentane of 0.01 to 3.0) with one or more catalyst compositions, including but not limited to the catalyst compositions described herein, to form cyclopentadiene at a temperature of 400° C. to 700° C., a partial pressure of 3 psia to about 100 psia at the reactor inlet (21 to 689 kPa-a), and a weight hourly space velocity of 1 $hr^{-1}$ to about 50 $hr^{-1}$.

The use of the catalyst compositions of this invention provides a conversion of at least about 10%, or at least about 20%, or at least about 30%, or in the range of from about 20% to about 50%, of said acyclic $C_5$ feedstock under acyclic $C_5$ conversion conditions of an n-pentane containing feedstock with equimolar $H_2$, a temperature in the range of from 400° C. to about 500° C., or about 450° C., an n-pentane partial pressure of about 5 psia (35 kPa-a), or about 7 psia (48 kPa-a), or from about 4 psia to about 6 psia at the reactor inlet (28 to 41 kPa-a), and an n-pentane weight hourly space velocity of about 2 $hr^{-1}$, or between 1 $hr^{-1}$ and 5 $hr^{-1}$.

The use of any one of the catalyst compositions of this invention provides a carbon selectivity to cyclic $C_5$ compounds of at least about 10%, or at least about 20%, or at least about 30%, or in the range from about 20% to about 50%, under acyclic $C_5$ conversion conditions including an n-pentane feedstock with equimolar $H_2$, a temperature in the range of about 400° C. to about 500° C., or about 450° C., an n-pentane partial pressure between 3 psia and 10 psia (21 to 69 kPa-a), and an n-pentane weight hourly space velocity between 10 $hr^{-1}$ and 20 $hr^{-1}$.

The use of any one of the catalyst compositions of this invention provides a carbon selectivity to cyclopentadiene of at least about 20%, or at least about 30%, or at least about 40%, or at least about 50%, or in the range from about 30% to about 50%, under acyclic $C_5$ conversion conditions including an n-pentane feedstock with equimolar $H_2$, a temperature in the range of about 550° C. to about 600° C., an n-pentane partial pressure of about 7 psia (48 kPa-a), or about 5 psia (35 kPa-a), or from about 4 psia to about 6 psia (28 to 41 kPa-a), and an n-pentane weight hourly space velocity of about 2 $hr^{-1}$, or between 1 $hr^{-1}$ and 5 $hr^{-1}$.

In the presence of the catalyst, a number of desired and undesirable side reactions may take place. The net effect of the reactions is the production of hydrogen and the increase of total volume (assuming constant total pressure). One particularly desired overall reaction (i.e., intermediate reaction steps are not shown) is:

n-pentane→CPD+3H$_2$.

Additional overall reactions include, but are not limited to:
n-pentane→1,3-pentadiene+2H$_2$,
n-pentane→1-pentene+H$_2$,
n-pentane→2-pentene+H$_2$,
n-pentane→2-methyl-2-butene+H$_2$,
n-pentane→cyclopentane+H$_2$,
cyclopentane→cyclopentene+H$_2$, or
cyclopentene→CPD+H$_2$.

Fluids inside the first reactor are essentially in gas phase. At the outlet of the first reactor, a first reactor hydrocarbon effluent, preferably in gas phase, is obtained. The first reactor hydrocarbon effluent may comprise a mixture of the following hydrocarbons, among others: heavy components comprising more than 8 carbon atoms such as multiple-ring aromatics; $C_8$, $C_7$, and $C_6$ hydrocarbons such as one-ring aromatics; CPD (the desired product); unreacted $C_5$ feedstock material such as n-pentane; $C_5$ by-products such as pentenes (1-pentene, 2-pentene, e.g.), pentadienes (1,3-pentadiene; 1,4-pentadiene, e.g.), cyclopentane, cyclopentene, 2-methylbutane, 2-methyl-1-butene, 3-methyl-1-butene, 2-methyl-1,3-butadiene, 2,2-dimethylpropane, and the like; $C_4$ by-products such as butane, 1-butene, 2-butene, 1,3-butadiene, 2-methylpropane, 2-methyl-1-propene, and the like; $C_3$ by-products such as propane, propene, and the like; $C_2$ by-products such as ethane and ethene, methane, and hydrogen.

The first reactor hydrocarbon effluent may comprise CPD at a concentration of C(CPD)1 wt %, based on the total weight of the $C_5$ hydrocarbons in the first reactor hydrocarbon effluent; and a1≤C(CPD)1≤a2, where a1 and a2 can be, independently, 15, 16, 18, 20, 22, 24, 25, 26, 28, 30, 32, 34, 35, 36, 38, 40, 45, 50, 55, 60, 65, 70, 75, 80, or 85 as long as a1<a2.

The first reactor hydrocarbon effluent may comprise acyclic diolefins at a total concentration of C(ADO)1 wt %, based on the total weight of the $C_5$ hydrocarbons in the first reactor hydrocarbon effluent; and b1≤C(ADO)1≤b2, where b1 and b2 can be, independently, 20, 18, 16, 15, 14, 12, 10, 8, 6, 5, 4, 3, 2, 1, or 0.5, as long as b1<b2. Preferably, 0.5≤C(ADO)≤10.

As a result of the use of the catalyst and the choice of reaction conditions in the first reactor, a high CPD to acyclic diolefin molar ratio in the first reactor hydrocarbon effluent can be achieved such that C(CPD)1/C(ADO)1≥1.5, preferably 1.6, 1.8, 2.0, 2.2, 2.4, 2.5, 2.6, 2.8, 3.0, 3.2, 3.4, 3.5, 3.6, 3.8, 4.0, 5.0, 6.0, 8.0, 10, 12, 14, 15, 16, 18, or 20. The high ratio of C(CPD)1/C(ADO)1 significantly reduces CPD loss as a result of Diels-Alder reactions between CPD and acyclic dienes in subsequent processing steps, and therefore, allows the processes of the present invention to achieve high DCPD yield and high DCPD purity for the subsequently produced DCPD fractions.

Desirably, the total absolute pressure and temperature of the first reactor hydrocarbon effluent should be maintained at levels such that the dimerization of CPD to form DCPD is substantially avoided, and the Diels-Alder reactions between CPD and acyclic dienes are substantially inhibited.

Because the overall conversion from acyclic $C_5$ hydrocarbons to CPD and hydrogen results in substantial volume increase (assuming constant total system pressure), a low partial pressure of CPD and/or a low partial pressure of hydrogen in the reaction mixture favors the conversion of acyclic $C_5$ hydrocarbons. The total partial pressure of $C_5$ hydrocarbons and hydrogen in the first reactor effluent at the outlet is desired to be lower than atmospheric pressure. Thus, where insufficient co-feedstock of a $C_1$-$C_4$ hydrocarbon or other co-feedstock is introduced into the first reactor, the total overall pressure of the first reactor effluent is desirably sub-atmospheric, in order to achieve a level of satisfactory conversion from acyclic $C_5$ hydrocarbons to CPD. However, direct separation of a sub-atmospheric stream has the disadvantage of potential oxygen/air ingress into the system, resulting in oxidation of CPD and other hydrocarbons and formation of undesirable species in the system. Thus, it is desirable that the first reactor hydrocarbon effluent is processed to a higher total pressure before separation thereof. Eductor systems, can be used for that purpose (as described in U.S. Ser. No. 62/250,708, filed Nov. 4, 2015).

Catalyst Regeneration

Over the course of the hydrocarbon conversion processes described herein, the activity of the catalyst generally gradually declines to form a deactivated catalyst due to the accumulation of carbonaceous or coke material and/or agglomeration of metal on the catalyst material during the reaction. As such, a regeneration cycle is advantageously performed to produce a regenerated catalyst having restored or substantially restored catalyst activity, typically by removing at least a portion of coke material from the catalyst composition. Preferably, regenerated catalyst has activity restored to at least 50% of the activity of the catalyst prior to deactivation, more preferably at least 60%, more preferably at least 80%. Regenerated catalyst also preferably has restored or substantially restored catalyst selectivity, e.g., selectivity restored to at least 50% of the selectivity of the catalyst prior to deactivation, more preferably at least 60%, more preferably at least 80%. Typically, a regeneration cycle is employed when the catalyst composition comprises >1 wt % coke, such as >5 wt % coke, such as >10 wt % coke, or even >20 wt % coke.

Regeneration is carried out in at least one regeneration zone. The regeneration zone(s) may be located in situ in the reaction zone or ex situ in one or more separate vessels apart from the reaction zone. Typically, in situ regeneration methods are employed when the reactor configuration of the hydrocarbon conversion process is a fixed bed system, such as a heated tubular reactor. Typically, regeneration is carried out in a separate regeneration zone when the reactor configuration of the hydrocarbon conversion process is a moving bed system, e.g., a circulating fluidized bed or a circulating settling bed.

A typical regeneration cycle begins by discontinuing contact of the hydrocarbon feedstock with the catalyst composition in the reaction zone or by transfer of the catalyst composition to a separate regeneration zone. Often, combustible hydrocarbon gas, including feedstock or reactor product, is purged from the catalyst composition using a purge gas, for example, N$_2$. Optionally, the purging step may be proceeded by a step of contacting the catalyst with a H$_2$ containing stream for partial, reductive removal of coke. The following regeneration steps, including at least oxychlorination and chlorine stripping, are then performed.

Regeneration of the catalyst material may occur as a continuous process or may be done batch wise. A regeneration cycle typically requires less than about 10 days, preferably less than about 3 days to complete. A regeneration cycle may be periodically performed between about once every 6 days to about once every 180 days, preferably between about once every 10 days to about once every 40 days.

I. Coke Removal

Generally, regeneration of the catalyst comprises a first step to remove deposited carbonaceous or coke material from the catalyst, i.e., a coke removal step. Coke removal can be performed by any process known in the art, including reductive and oxidative removal methods. Reductive removal is preferably performed by contacting the catalyst with a gaseous stream comprising hydrogen under conditions effective to remove at least a portion of coke from the catalyst. Oxidative removal is preferably performed by contacting the catalyst with a gaseous stream comprising an oxygen source, and optionally a chlorine source, under conditions effective to remove at least a portion of coke from the catalyst. A preferred oxygen source is air, which is preferably diluted to reduce the $O_2$ concentration to between about 0.5 mol % and about 10 mol %. During coke removal, at least a portion of the Group 10 metal may be converted to a metal oxide. Thus, after coke removal at least a portion of the Group 10 metal is typically present in reduced form and/or as a metal oxide.

Often, at least 10 wt % (≥10 wt %) of coke material present at the start of the coke removal step is removed, such as between about 10 wt % to about 100 wt %. Preferably, between about 90 wt % to about 100 wt % of coke material is removed.

II. Oxychlorination

The harsh conditions, e.g. high temperature, employed during coke removal typically result in agglomeration of the Group 10 metal particles and at least partial removal of the Group 10 metal particles from the pores of the crystalline aluminosilicate. Generally, regeneration of the catalyst comprises an oxychlorination step subsequent to coke removal under conditions effective for dispersing at least a portion of the at least one Group 10 metal on the surface of the catalyst. For purposes of the disclosure, "catalyst surface" specifically includes area within the microporous structure of the catalyst composition.

Generally, the oxychlorination step is further effective to convert at least a portion of the Group 10 metal present in reduced and/or metal oxide to produce a Group 10 metal chlorohydrate. Typically, the Group 10 metal chlorohydrate can be represented by Formula I:

[M(OH)$_x$Cl$_y$]$^a$  Formula I wherein M is a Group 10 metal, x is an integer ranging from 0 to 4, y is an integer ranging from 2 to 6, wherein the sum of x and y ranges from 4 to 6, and wherein a is an integer ranging from −2 to 0. Without wishing to be bound by theory, it is believed that the metal chlorohydrate of Formula I is a mobile species that can relocate to different binding sites of the support. This relocation is believed to effectively decrease the average Group 10 metal particle size and increases the total Group 10 metal surface area (i.e., available active sites), regenerating the catalyst activity.

The oxychlorination step typically comprises contacting the catalyst with a gaseous stream comprising a chlorine source and an oxygen source. The chlorine source may be selected from the group consisting of HCl, Cl$_2$, chlorinated hydrocarbons, e.g., CHCl$_3$, C$_2$H$_4$Cl$_2$, or C$_3$H$_6$Cl$_2$, and mixtures thereof, preferably HCl and/or Cl$_2$. In any embodiment, the chlorine source may be present in the gaseous stream at a concentration ranging from about 10 vppm to about 50,000 vppm based on the total volume of the gaseous stream, such as about 100 to about 30,000 vppm, preferably from about 500 vppm to about 20,000 vppm. A preferred oxygen source is air, which is preferably diluted to reduce the $O_2$ concentration to between about 0.5 mol % and about 10 mol %. Often, the gaseous stream further comprises water at a concentration of about 500 to about 20,000 vppm based on the total volume of the gaseous stream. Typically, at least a portion of, typically a majority of, e.g, 50 vol % or more, preferably 80 vol % of more, ideally 90 vol % or more, e.g., 100 vol % of the gaseous stream employed during oxychlorination is withdrawn from the regeneration zone to form an effluent.

Oxychlorination can be conducted under any combination of process conditions effective for dispersing at least a portion of the at least one Group 10 metal on the surface of the catalyst and for producing a Group 10 metal chlorohydrate. Preferred temperature and pressure conditions include a temperature ranging from about 400° C. to about 750° C., more preferably from about 450° C. to about 550° C.; and a total pressure ranging up to about 100 bar, e.g., from about 0.1 bar to about 100 bar, more preferably from about 1 bar to about 10 bar, ideally at or about atmospheric pressure. Preferred flow rate conditions for the chlorine source and the oxygen source in the gaseous stream are those resulting in the following preferred partial pressure ranges in the effluent: a base 10 logarithm of chlorine partial pressure (log (PCl$_2$)) in the range from about −15.0 to about 5.0, more preferably from about −5.0 to about 3.0; and a base 10 logarithm of oxygen partial pressure (log(PO$_2$)) ranging from about −5.0 to about 2.0, more preferably from about −3.0 to 1.0.

Preferably, each component of the gaseous stream is fed to the regeneration zone within about 30% of its chemical equilibrium concentration, more preferably within about 20% of its chemical equilibrium concentration. Particularly preferably, the gaseous stream comprises a mixture of oxygen, HCl, Cl$_2$, and H$_2$O, wherein each of these mixture components is fed to the regeneration zone within about 20% of its chemical equilibrium concentration. The reversible reaction and equilibrium constant expression governing the equilibrium concentrations of these components are as follows:

$$2H_2O + 2Cl_2 \xrightleftharpoons{K_{eq}} O_2 + 4HCl$$

$$K_{eq} = \frac{P_{HCl}^4 P_{O_2}}{P_{H_2O}^2 P_{Cl_2}^2 P_{std}}$$

wherein $K_{eq}$ can be determined as a function of temperature in accordance with the following equation:

$\ln(K_{eq})=16.4-14343(1/T)+89524*(1/T)^2$.

The preferred component concentration ranges for equilibrium mixtures of O$_2$, HCl, H$_2$O, and Cl$_2$ at 550° C. is shown in Table 1.

TABLE 1

| | O$_2$ (vol %) | HCl (vppm) | Cl$_2$ (vppm) | H$_2$O (vppm) |
|---|---|---|---|---|
| High | 20 | 10000 | 10000 | 20000 |
| Low | 2 | 500 | 500 | 500 |

Often, at least a portion of the effluent withdrawn during the oxychlorination step is recycled to the regeneration zone. Where the gaseous stream comprises a mixture of oxygen, HCl, Cl$_2$, and H$_2$O, a portion of HCl and/or H$_2$O is typically removed from the recycled portion of the effluent prior to supplying the recycled stream to the regeneration zone. Additionally, or alternatively, supplemental $O_2$ and/or $Cl_2$ may be added to the recycled portion of the effluent prior to supplying the recycled stream to the regeneration zone.

III. Chlorine Stripping

In conventional regeneration methods for high Group 10 metal-to-aluminum content catalyst materials, the catalyst is typically subjected to a reduction step immediately following oxychlorination. It has presently been found that the activity of the regenerated catalyst compositions of this disclosure can be improved by employing a chlorine stripping step subsequent to oxychlorination under conditions effective for increasing the O/Cl ratio of the Group 10 metal chlorohydrate. By increasing the O/Cl ratio of the Group 10 metal chlorohydrate, it is meant that the chlorine content of the metal chlorohydrate is reduced and the oxygen concentration of the metal chlorohydrate is increased. For example, with reference to the metal chlorohydrate of Formula I, increasing the O/Cl ratio refers to increasing the value of x and decreasing the value of y.

Typically, the chlorine stripping step converts the first metal chlorohydrate of Formula I to produce a second metal chlorohydrate of Formula II:

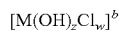  Formula II wherein M is a Group 10 metal, z is an integer ranging from 2 to 5, w is an integer ranging from 1 to 4, wherein the sum of z and w ranges from 4 to 6, and wherein b is an integer ranging from −2 to 0, wherein z>x and wherein w<y. Typically, z may be greater than x by an integer ranging from 1 to 5, and w may be less than y by an integer ranging from 1 to 5. For example, z may be greater than x by an integer of 1, 2, or 3, while w may be less than y by an integer of 1, 2, or 3. Without wishing to be bound by theory, it is believed that the metal chlorohydrate of Formula II is has higher surface affinity than the metal chlorohydrate of Formula I, resulting in higher dispersion of the Group 10 metal upon reduction performed subsequent to oxychlorination.

The chlorine stripping step typically comprises contacting the catalyst with a gaseous stream comprising an oxygen source, optionally in combination with a chlorine source and/or a water source. The chlorine source may be selected from the group consisting of HCl, $Cl_2$, chlorinated hydrocarbons, e.g., $CHCl_3$, $C_2H_4Cl_2$, or $C_3H_6Cl_2$, and mixtures thereof, preferably HCl and/or $Cl_2$. A preferred oxygen source is air, which is preferably diluted to reduce the $O_2$ concentration to between about 0.5 mol % and about 10 mol %. Often, the gaseous stream employed during chlorine stripping has the same composition as the gaseous stream employed during oxychlorination. As described below, in such aspects the temperature and/or total pressure is adjusted to achieve the desired O/Cl ratio increase. Typically, at least a portion of, typically a majority of, e.g, 50 vol % or more, preferably 80 vol % of more, ideally 90 vol % or more, e.g., 100 vol %, of the gaseous streams present in the regeneration zone during chlorine stripping is withdrawn from the regeneration zone to form an effluent.

Chlorine stripping can be conducted under any combination of process conditions effective for increasing the O/Cl ratio of the Group 10 metal chlorohydrate. Preferred temperature and pressure conditions include a temperature ranging from about 400° C. to about 750° C., more preferably from about 450° C. to about 550° C.; and a total pressure ranging up to about 100 bar, e.g., from about 0.1 bar to about 100 bar, more preferably from about 1 bar to about 10 bar, ideally at or about atmospheric pressure. Preferred flow rate conditions for the oxygen source and the optional chlorine source in the gaseous stream are those resulting in the following preferred partial pressure ranges in the effluent: $\log(PCl_2)$ in the range from about −15.0 to about 5.0, more preferably from about −5.0 to about 3.0; and $\log(PO_2)$ ranging from about −5.0 to about 2.0, more preferably from about −3.0 to 1.0. In aspects where the gaseous stream employed during chlorine stripping has the same composition as the gaseous stream employed during oxychlorination, chlorine stripping is typically conducted at the same or similar process conditions as oxychlorination with the exception that the temperature is typically reduced by about 20° C. to about 200° C. Following chlorine stripping, purge gas, e.g. $N_2$, is generally reintroduced to purge oxidant gases from the regeneration zone.

IV. Reduction & Sulfidation

After chlorine stripping and purging, the catalyst is generally chemically reduced to convert the Group 10 metal to elemental form. Preferably, this reduction is achieved by contacting the catalyst with a gaseous stream comprising from about 10 vol % to about 100 vol % hydrogen at a temperature within the range of about 100° C. to about 650° C. The gaseous stream preferably contains less than about 100 vppm, more preferably less than about 10 vppm, of each of the following components: CO, $CO_2$, $H_2O$, and/or hydrocarbon.

Optionally, the reduced catalyst is sulfided by contacting the catalyst with a sulfur containing gaseous stream. Typically, the sulfur containing gaseous stream has a sulfur concentration of about 100 to about 1,000 vppm. A preferred sulfur containing gaseous stream is a mixture of $H_2S$ and $H_2$. The sulfur containing gaseous stream is generally contacted with the catalyst at a flow rate and period of time sufficient to deposit from about 10 to about 1,000 ppm by weight of S on the catalyst.

Following reduction and optional sulfidation, the regeneration cycle is complete and flow of hydrocarbon feedstock may be resumed for fixed bed systems or the catalyst transferred back to the reaction zone for moving bed systems.

Catalyst Rejuvenation

The hydrocarbon conversion processes may further comprise periodically performing one or more rejuvenation cycles to remove at least a portion of incrementally deposited coke material accumulated on the catalyst material. As used herein, "incrementally deposited coke" refers to the amount of coke that is deposited on the catalyst during a conversion cycle. Typically, a rejuvenation cycle is employed when the catalyst composition comprises >1 wt % incrementally deposited coke, such as >5 wt % incrementally deposited coke, or >10 wt % incrementally deposited coke.

A rejuvenation cycle may be advantageously performed ≥10 minutes, e.g., ≥30 minutes, ≥2 hours, ≥5 hours, ≥24 hours, ≥2 days, ≥5 days, ≥20 days, after beginning the specified hydrocarbon conversion process. Advantageously, performing a rejuvenation cycle lengthens the amount of time the catalyst can maintain adequate activity before the next regeneration cycle. Accordingly, the hydrocarbon conversion processes may comprise ≥1 e.g., ≥2, ≥5 or ≥20 rejuvenation cycles between each regeneration cycle.

Rejuvenation is carried out in at least one rejuvenation zone. The rejuvenation zone(s) may be located in situ in the reaction zone or ex situ in one or more separate rejuvenation zones apart from the reaction zone. Typically, in situ rejuvenation methods are employed when the reactor configuration of the hydrocarbon conversion process is a fixed bed system, such as a heated tubular reactor. Typically, rejuvenation is carried out in a separate rejuvenation zone when the reactor configuration of the hydrocarbon conversion process is a moving bed system, e.g., a circulating fluidized bed or a circulating settling bed.

A typical rejuvenation cycle begins by discontinuing contact of the hydrocarbon feedstock with the catalyst composition in the reaction zone or by transfer of the catalyst composition to a separate rejuvenation zone. Often, combustible hydrocarbon gas, including feedstock or reactor product, is purged from the catalyst composition using a purge gas, for example, $N_2$. Optionally, the purging step may be proceeded by a step of contacting the catalyst with a $H_2$ containing stream for partial, reductive removal of coke.

After purging, rejuvenation of the catalyst is preferably achieved using a mild oxidation step, and optionally at least one hydrogen treatment. The mild oxidation step generally comprises contacting the catalyst composition with an oxygen-containing gaseous stream under conditions effective to remove at least a portion of incrementally deposited coke material on the catalyst. Typically, these conditions include a temperature range of about 250° C. to about 500° C., and a total pressure of about 0.1 bar to about 100 bar, preferably at or about atmospheric pressure. Further, the oxygen-containing gaseous stream is typically supplied to the rejuvenation zone(s) at a total WHSV in the range from about 1 to about 10,000. The source of oxygen may be, for example, $O_2$, $O_3$, nitrogen oxides, $CO_2$, and mixtures of any of the foregoing. Typically, the concentration of oxygen in the gaseous stream is in the range from about 0.1 to about 20% by volume for $O_2$, $O_3$, and/or nitrogen oxides, preferably from about 0.5 to about 5%. When $CO_2$ is utilized, higher concentration may be utilized, up to 100%; lower levels of the other oxidants may be utilized sequentially with $CO_2$ and/or blended into $CO_2$. The oxygen-containing gaseous stream may further comprise a non-reactive substance (e.g., $N_2$, CO). Following rejuvenation, purge gas, e.g. $N_2$, is generally reintroduced to purge oxidant gases from the rejuvenation zone.

Following rejuvenation and purging, the catalyst is typically reduced to convert the noble metal oxide formed during rejuvenation to the elemental metal. Subsequent to reduction, the rejuvenation cycle is complete and flow of hydrocarbon feedstock may be resumed or the catalyst transferred back to the reaction zone.

Typically, rejuvenation is effective at removing at least 10 wt % (≥10 wt %) of incrementally deposited coke material. Between about 10 wt % to about 100 wt %, preferably between about 90 wt % to about 100 wt % of incrementally deposited coke material is removed.

Products and Articles

The process for producing cyclic $C_5$ compounds of this invention comprises one or more cyclic $C_5$ compositions. Such composition comprises one or more cyclic $C_5$ compounds. These cyclic $C_5$ compounds include and are selected from the group consisting of cyclopentadiene, dicyclopentadiene, cyclopentene, cyclopentane, pentene, pentadiene, and mixtures of two or more thereof.

The cyclic $C_5$ compounds may be reacted with a substrate to form a product. In some embodiments, the substrate comprise a double bond. Such product includes is one or more of a Diels Alder reaction derivative of cyclopentadiene, cyclic olefin copolymers, cyclic olefin polymers, polycyclopentene, ethylidene norbornene, EPDM rubber, alcohols, plasticizers, blowing agents, solvents, octane enhancers, gasoline, unsaturated polyester resins, hydrocarbon resin tackifiers, formulated epoxy resins, polydicyclopentadiene, metathesis polymers of norbornene or substituted norbornenes or dicyclopentadiene, tetracyclodocene, or any combination of two or more thereof. The Diels Alder reaction derivatives of cyclopentadiene is or comprises norbornene or substituted norbornenes.

The product may be made into a useful article. Such article comprise any of the products made or derived from the process of this invention. Particularly, the article may be one or more of wind turbine blades, composites containing glass or carbon fibers, and formulated adhesives.

The following examples illustrate the present invention. Numerous modifications and variations are possible and it is to be understood that within the scope of the appended claims, the invention may be practiced otherwise than as specifically described herein.

EXAMPLES

Analytic Test Method—Hydrogen Chemisorption

Pulse $H_2$ chemisorption was performed at 35° C. on a Micromeritics Autochem 2920 analyzer. The sample (0.10-0.15 g) was pretreated in Ar (50 cm$^3$ min$^{-1}$) at 250° C. for 30 min and then reduced in 10% $H_2$/Ar (50 cm$^3$ min$^{-1}$) at 500° C. for 30 min Afterwards, 0.5050 cm$^3$ of 10 vol. % $H_2$/Ar was pulsed over the catalyst bed every 4 min. Platinum dispersion was calculated from the amount of chemisorbed $H_2$ on the basis of an atomic surface density of $1.25 \times 10^{19}$ atoms m$^{-2}$ and an adsoprtion stoichiometry of Pt/$H_2$=2.

Analytic Test Method—Carbon Monoxide Chemisorption

Pulse CO chemisorption was performed at 35° C. on a Thermo Scientific TPDRO 1100 instrument. The sample was first reduced in 5% $H_2$/$N_2$ (20 mL/min) at 250° C. for 15 minutes. The sample (~0.1 g) was then placed in a temperature controlled chamber set at 35° C. Afterwards, 20% CO/He (~10 micromoles of CO) was pulsed over the sample (10 pulses with 7 minute interval between pulses). Pulses were detected by a thermal conductivity detector, with a moisture trap placed between the sample and the detector to collect any moisture. Typically, 2 to 3 pulses of the 10 total pulses yielded CO uptake measurements, and the final 6 pulses were full pulses used to determine an internal calibration factor to take into account variances in room temperature and pressure. The determined internal calibration factor was then used to convert the observed peak areas into the number of micromoles of CO.

Example 1—ZSM-5 Catalyst Composition Synthesis

A synthesis mixture with ~22% solids was prepared from 8,800 g of deionized (DI) water, 600 g of 50% NaOH solution, 26 g of 43% Sodium Aluminate solution, 730 g of n-propyl amine 100% solution, 40 g of ZSM-5 seed crystals, and 3,190 g of Ultrasil PM™ modified silica were mixed in a 5-gal pail container and then charged into a 5-gal autoclave after mixing. The synthesis mixture had the following molar composition:

$SiO_2$/$Al_2O_3$ ~470
$H_2O$/$SiO_2$ ~12.1
OH/$SiO_2$ ~0.16
Na/$SiO_2$ ~0.16
n-PA/Si ~0.25.

The synthesis mixture was mixed and reacted at 230° F. (110° C.) at 350 rpm for 48 hours. The resulting reaction slurry was discharged and stored in a 5-gal pail container. The XRD pattern of the as-synthesized material showed the typical pure phase of ZSM-5 topology. The SEM of the as-synthesized material shows that the material was composed of mixture of large crystals with size of ~1-2 micron. The resulting ZSM-5 crystals had a $SiO_2/Al_2O_3$ molar ratio of ~498, total surface area(SA)/(micropore SA+mesopore SA) of 468 (422+45) $m^2/g$, and a sodium content of ~0.37 wt %.

A portion of the synthesized material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~5015 ppm Pt was added via incipient wetness impregnation using an aqueous solution of tetraamine platinum hydroxide. The resulting catalyst composition was dried overnight at 250° F. (121° C.), and lastly calcined in air at 610° F. (321° C.) for 1 hour. The catalyst composition powder was pressed, crushed, and sieved to obtain 20-40 mesh particle size.

Example 2—Sintering and Regeneration of Example 1 Catalyst Composition

The synthesized ZSM-5 catalyst composition of Example 1 was sintered at 650° C. for 2 hours under flowing air to induce Pt agglomeration on the zeolite support. As shown in Table 2 below, the sintered material exhibited a 35% decrease in CO uptake from that of the fresh catalyst, demonstrating the expected decrease in active sites resulting from agglomeration of the noble metal.

A sample of the sintered material was regenerated by a two-step procedure comprising an oxychlorination step followed by a chlorine stripping step, while a second sample was regenerated via oxychlorination in the absence of a subsequent chlorine stripping step. In each instance, the oxychlorination step was performed by holding the material at 550° C. for 1 hour under flowing air and 1,2-dichloropropane (DCP, 40 μL/h). The chlorine stripping step was performed by calcining the oxychlorinated material in air at 550° C. for 1 hour. The regenerated catalyst samples were then cooled in air to room temperature over 4 hours and reduced in the presence of hydrogen.

CO uptake values of the reduced catalyst were measured for the sample regenerated via oxychlorination alone and the sample regenerated via oxychlorination with the addition of a chlorine stripping step. These values were compared to those of the fresh and sintered materials, as shown in Table 2.

TABLE 2

|  | CO:Pt |
| --- | --- |
| Fresh | 1.32 |
| Sintered | 0.86 |
| Regenerated (Oxychlorination Only) | ~0 |
| Regenerated (Oxychlorination & Chlorine Stripping) | 1.04 |

Table 2 shows that the two-step regeneration procedure, comprising oxychlorination followed by chlorine stripping, resulted in a 21% increase in CO uptake as compared to the sintered material. These data indicate that the oxychlorination was successful in redispersing the platinum particles via formation of a mobile platinum chlorohydrate species, increasing the available active sites.

Table 2 further shows that the oxychlorinated material that was not subjected to a chlorine stripping step did not adsorb CO at an appreciable level. These data suggest that platinum reagglomerates in the oxychlorinated material in the absence of the chlorine stripping step, resulting in severely limited CO uptake. Without wishing to be bound by theory, it is believed that the chlorine stripping step prevents platinum reagglomeration by increasing the O/Cl ratio of the platinum chlorohydrate, thereby reducing or eliminating the highly mobile Pt—Cl chlorohydrate species.

Example 3—On-Oil Testing of Catalyst Composition of Examples 1-2

Samples of the fresh, sintered, and oxychlorinated catalyst composition of Examples 1-2 were evaluated for performance via the following procedure. The catalyst composition (0.5 g) was physically mixed with quartz (1.5 g, 60-80 mesh) and loaded into a reactor having a ⅜" (0.95 cm) outer diameter and an 18" (46 cm) length. The catalyst composition was dried for 1 hour under He (100 ml/min, 30 psig (207 kPa), 250° C.) then reduced for 1 hour under $H_2$ (200 mL/min, 30 psig (207 kPa), 500° C.). The catalyst composition was then tested for performance with a feed of n-pentane, $H_2$, and balance He, typically at 550-600° C., 5.0 psia (35 kPa-a) $C_5H_{12}$, 1.0 molar $H_2:C_5H_{12}$, 14.7 $hr^{-1}$ WHSV, and 30 psig (207 kPa) total. Catalyst composition stability and regenerability were tested post initial tests at 550 to 600° C. by treatment with $H_2$ (200 mL/min, 30 psig (207 kPa), 650° C.) for 5 hours then retesting performance at 600° C.

FIG. 1 shows the total cyclo-product (cyclopentane, cyclopentene, and cyclopentadiene) yield for the fresh, sintered, and oxychlorinated catalyst. Yield was not demonstrated to be a strong function of CO:Pt in this range, but the data show that Pt can be re-dispersed via oxychlorination, and that the resultant material is still very active for CPD production.

Example 4—Extrudate Catalyst Composition Synthesis Having Platinum-to-Copper Molar Ratio Target of 1:1

A synthesis mixture with ~22% solids was prepared from 8,800 g of deionized (DI) water, 600 g of 50% NaOH solution, 26 g of 43% Sodium Aluminate solution, 730 g of n-propyl amine 100% solution, 20 g of ZSM-5 seed crystals, and 3,190 g of Sipernat™ 340 specialty silica were mixed in a 5-gal pail container and then charged into a 5-gal autoclave after mixing. The synthesis mixture had the following molar composition:

$SiO_2/Al_2O_3$ ~470
$H_2O/SiO_2$ ~10.7
$OH/SiO_2$ ~0.16
$Na/SiO_2$ ~0.16
n-PA/Si ~0.25.

The synthesis mixture was mixed and reacted at 210° F. (99° C.) at 350 rpm for 72 hours. The resulting reaction slurry was discharged and stored in a 5-gal pail container. The XRD pattern of the as-synthesized material showed the typical pure phase of ZSM-5 topology. The SEM of the as-synthesized material showed that the material was composed of mixture of crystals with size of ~0.5-1 micron. The resulting ZSM-5 crystals had a $SiO_2/Al_2O_3$ molar ratio of ~467 and a sodium content of ~0.25 wt %.

An aqueous mixture was prepared for extrusion using 65 wt % of the as-synthesized zeolite support and 35 wt % of a silica binder composed of 50 wt % Ludox™ LS silica and 50 wt % Aerosil™ 200 silica. This mixture was extruded into 1/16" (0.16 cm) diameter cylinders and dried. This extrudate was then calcined for 6 hours in nitrogen at 900° F. (480° C.). After cooling, the sample was re-heated to 900° F. (480° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F. (540° C.), the oxygen content was increased to 16.8%, and the material was held at 1000° F. (540° C.) for 6 hours. After cooling, 0.27 wt % Cu was added via incipient wetness impregnation using an aqueous solution of copper nitrate. The sample was dried for four hours at 250° F. (121° C.). Subsequently, 0.30 wt % Pt was added via incipient wetness impregnation using an aqueous solution of tetraamine platinum nitrate. The catalyst was dried in air at room temperature for 3 hours then at 250° F. (121° C.) for 2.5 hours and lastly calcined in air for three hours at 660° F. (321° C.). The catalyst composition extrudate was crushed and sieved to obtain 20-40 mesh particle size.

Example 5—Sintering and Regeneration of Example 4 Catalyst Composition

The synthesized extrudate catalyst composition of Example 4 was sintered at 700° C. for 4 hours under flowing air to induce Pt agglomeration on the zeolite support. As shown in Table 3 below, the sintered material exhibited a 70% decrease in hydrogen chemisorption from that of the fresh catalyst, demonstrating the expected decrease in active sites resulting from agglomeration of the noble metal.

The sintered material was regenerated by a two-step procedure comprising an oxychlorination step followed by a chlorine stripping step. Prior to oxychlorination, the sintered material (0.25 g) was dried in flowing nitrogen (800 ml/min, 40 psia (280 kPa)) at 250° C. for 2 hours. The temperature was then ramped to the desire oxychlorination temperature (500° C. or 550° C.) over 2 hours in nitrogen. Oxychlorination was performed by continuously feeding an oxychlorination mixture comprising $O_2$, HCl, $Cl_2$, and $H_2O$ over the sintered material for 1 hour under a variety of conditions, as shown in Table 3. Chlorine stripping was performed by flowing an oxygen-containing gaseous stream comprising 2 vol % oxygen over the oxychlorinated catalyst at the oxychlorination temperature for 30 minutes. Nitrogen (800 ml/min, 40 psia (280 kPa)) was then flowed over the catalyst at 500° C. to purge the material prior to reducing the material in flowing hydrogen (500 ml/min) at 500° C. for 4 hours.

TABLE 3

| Run | HCl (ppm) | $Cl_2$ (ppm) | $O_2$ (vol %) | $H_2O$ (ppm) | Temp (° C.) | HCl (psia) | $Cl_2$ (psia) | $O_2$ (psia) | $H_2O$ (psia) | Total Pressure (psia) | H:Pt |
|---|---|---|---|---|---|---|---|---|---|---|---|
| Fresh | | | | | | | | | | | 0.70 |
| Sintered | | | | | | | | | | | 0.21 |
| 1 | 5993 | 4838 | 10.00 | 10290 | 500 | 0.24 | 0.19 | 3.97 | 0.41 | 40 | 0.23 |
| 2 | 7122 | 4221 | 9.95 | 9655 | 550 | 0.28 | 0.17 | 3.98 | 0.39 | 40 | 0.03 |
| 3 | 3015 | 2526 | 10.00 | 4987 | 500 | 0.12 | 0.10 | 3.97 | 0.20 | 40 | 0.27 |
| 4 | 3601 | 2224 | 9.94 | 4661 | 550 | 0.14 | 0.09 | 3.97 | 0.19 | 40 | 0.14 |
| 5 | 3131 | 1907 | 5.00 | 5038 | 500 | 0.12 | 0.08 | 1.99 | 0.20 | 40 | 0.13 |
| 6 | 3655 | 1589 | 4.97 | 4714 | 550 | 0.15 | 0.06 | 1.99 | 0.19 | 40 | 0.12 |
| 7 | 3023 | 1259 | 10.00 | 10063 | 500 | 0.12 | 0.05 | 3.97 | 0.40 | 40 | 0.1 |
| 8 | 3484 | 1003 | 9.93 | 9765 | 550 | 0.14 | 0.04 | 3.97 | 0.39 | 40 | 0.13 |
| 8 | 5395 | 4932 | 5.00 | 5783 | 500 | 0.21 | 0.20 | 1.99 | 0.23 | 40 | 0.21 |
| 10 | 6351 | 4393 | 4.99 | 5239 | 550 | 0.25 | 0.18 | 1.99 | 0.21 | 40 | 0.27 |
| 11 | 4635 | 4937 | 10.00 | 6030 | 500 | 0.18 | 0.20 | 3.97 | 0.24 | 40 | 0.27 |
| 12 | 5503 | 4445 | 9.94 | 5503 | 550 | 0.22 | 0.18 | 3.98 | 0.22 | 40 | 0.11 |
| 13 | 3252 | 1030 | 5.00 | 10063 | 500 | 0.13 | 0.04 | 1.99 | 0.40 | 40 | 0.22 |
| 14 | 3695 | 792 | 4.97 | 9766 | 550 | 0.15 | 0.03 | 1.99 | 0.39 | 40 | 0.01 |
| 15 | 6262 | 3814 | 5.00 | 10076 | 500 | 0.25 | 0.15 | 1.99 | 0.40 | 40 | 0.16 |
| 16 | 7335 | 3219 | 4.99 | 9446 | 550 | 0.29 | 0.13 | 1.99 | 0.38 | 40 | 0.03 |

As seen from Table 3, the oxychlorination conditions of runs 3 and 11 yielded the best chemisorption results, as the measured value of H:Pt in each of the regenerated materials of these runs increased from the sintered value of 0.21 up to 0.27.

Example 6—On-Oil Testing of Example 5 Catalyst Composition

Two samples of regenerated catalyst composition were prepared to replicate the materials of Example 5 that were oxychlorinated in accordance with the conditions of runs 3 (Sample A) and 11 (Sample B).

These two regenerated Samples A & B, in addition to a sample of the sintered material of Example 5 (Sample C), conditions were evaluated for performance via the following procedure. The catalyst composition (0.38 g) was physically mixed with quartz (1.5 g, 60-80 mesh) and loaded into a reactor having a 3/8" (0.95 cm) outer diameter and an 18" (46 cm) length. The catalyst composition was dried for 1 hour under He (100 mL/min, 30 psig (207 kPa), 250° C.) then reduced for 1 hour under $H_2$ (200 mL/min, 30 psig (207 kPa), 500° C.). The catalyst composition was then tested for performance with a feed of n-pentane, $H_2$, and balance He, at 575° C., 7.0 psia (48 kPa-a) $C_5H_{12}$, 1.0 molar $H_2:C_5H_{12}$, 30 hr$^{-1}$ WHSV, and 60 psia (410 kPa) total.

Figure 2:
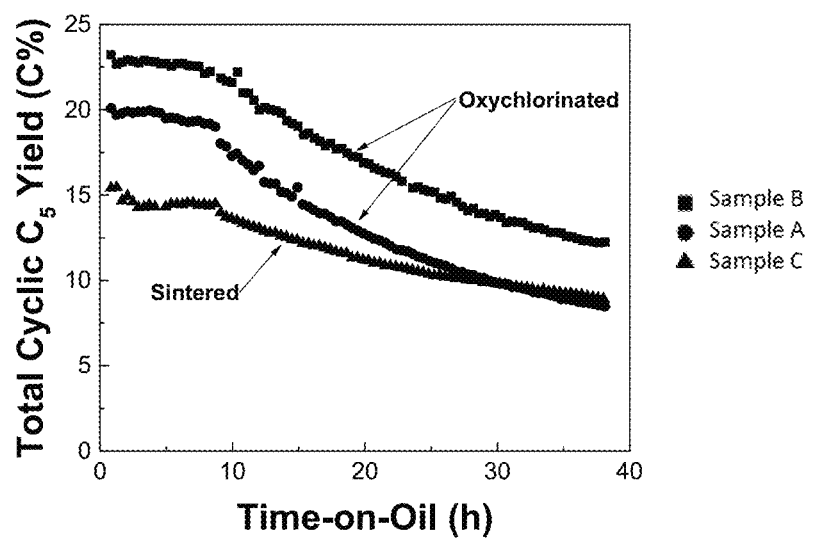
FIG. 2 shows the yield of cyclic $C_5$ against time-on-oil resulting from the performance evaluation of sintered and regenerated catalyst compositions conducted in Example 6.

FIG. 2 shows the total cyclic $C_5$ yield for the sintered (Sample C) and both regenerated catalysts (Samples A & B) against time-on-oil. Cyclization activity was regenerated to 130% and 150% of the original, sintered activity.

Example 7—ZSM-5/Pt/Rh Catalyst Composition Synthesis

A sample of the zeolite support material synthesized in Example 1 in sodium form was calcined for 6 hours in nitrogen at 900° F. (482° C.). After cooling, the sample was re-heated to 900° F. (482° C.) in nitrogen and held for 3 hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.23 wt % Rh was added via incipient wetness impregnation using an aqueous solution of rhodium(III) nitrate hydrate. The Rh impregnated catalyst was dried at 250° F. (121° C.) for 4 hours. Subsequently, ~0.53 wt % Pt was added via incipient wetness impregnation using an aqueous solution of tetraamine platinum hydroxide. The resulting catalyst composition was dried at 250° F. (121° C.) for ~18 hours, and lastly calcined in air at 610° F. (321° C.) for 1 hour. The catalyst composition powder was pressed, crushed, and sieved to obtain 20-40 mesh particle size.

Example 8—ZSM-5/Pt/La Catalyst Composition Synthesis

A sample of the zeolite support material synthesized in Example 1 in sodium form was calcined for 6 hours in nitrogen at 900° F. (482° C.). After cooling, the sample was re-heated to 900° F. (482° C.) in nitrogen and held for 3 hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.34 wt % La was added via incipient wetness impregnation using an aqueous solution of lanthanum nitrate hexahydrate. The La impregnated catalyst was dried at 250° F. (121° C.) for 4 hours. Subsequently, ~0.50 wt % Pt was added via incipient wetness impregnation using an aqueous solution of tetraamine platinum hydroxide. The resulting catalyst composition was dried at 250° F. (121° C.) for ~23 hours, and lastly calcined in air at 610° F. (321° C.) for 1 hour. The catalyst composition powder was pressed, crushed, and sieved to obtain 20-40 mesh particle size.

Example 9—Oxychlorination and Chlorine Stripping of Catalyst Compositions of Examples 7-8

Fresh Rh and La containing Pt/ZSM-5 catalysts of Examples 7 and 8, respectively, were subjected to oxychlorination and chlorine stripping steps in accordance with the following procedure to test the regenerability of these materials.

The material (0.25 g) was mixed with SiC (5 g) and loaded into a 0.56" (1.4 cm) ID, 33.5" (85 cm) long quartz reactor. The catalyst was dried in flowing nitrogen (800 sccm, 40 psia (280 kPa)) over 2 hours at 250° C. The temperature was then ramped to 500° C. over 2 hours in nitrogen. Oxychlorination was performed by continuously feeding an oxychlorination mixture comprising $O_2$ (10 vol %, 3.97 $P_{O2}$), HCl (2800 ppm, 0.11 $P_{HCl}$), $Cl_2$ (2200 ppm, 0.09 $P_{CL2}$) and $H_2O$ (5000 ppm, 0.20 $P_{H2O}$) over the material for 1 hour at 500° C. Chlorine stripping was performed by flowing an oxygen-containing gaseous stream comprising 2 vol % oxygen over the oxychlorinated catalyst at the oxychlorination temperature for 30 minutes. Nitrogen (800 ml/min, 40 psia (280 kPa)) was then flowed at 500° C. to purge the material prior to reducing the material in flowing hydrogen (500 ml/min) at 500° C. for 4 hours.

Example 10—On-Oil Testing of Catalyst Compositions of Examples 7-9

Samples of the fresh and treated (i.e., subjected to oxychlorination and chlorine stripping) catalyst compositions of Examples 7-9 were evaluated for performance via the following procedure. The catalyst sample (0.2-0.8 g) was physically mixed with an appropriate amount of high-purity SiC (40-60 mesh) and loaded into a reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks. The catalyst samples were dried for 2 hours under He (200 mL/min, 60 psia, 250° C.) then reduced for 4 hour under $H_2$ (200 mL/min, 60 psia, 500° C.).

A feed consisting of 7.0 psia n-pentane, 7.0 psia $H_2$ and balancing He was introduced to the catalyst bed. The total pressure was 60 psia. The catalyst was de-edged at 550° C. for 8 hours at a WHSV of 3000 (g n-pentane/g Pt $h^{-1}$) and then tested at 575° C. for 24 hours at a WHSV of 6000 (g n-pentane/g Pt $h^{-1}$).

Figure 3A:
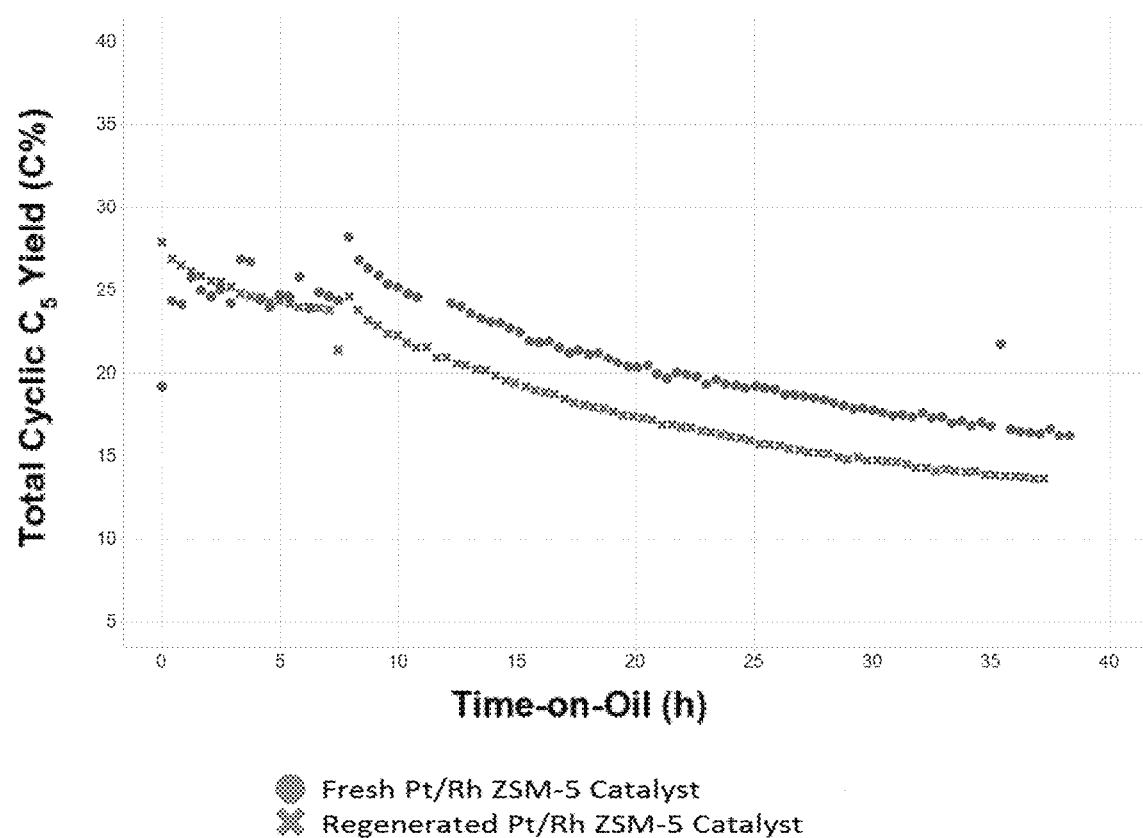
FIG. 3A and FIG. 3B show the yield of cyclic $C_5$ against time-on-oil resulting from the performance evaluation of fresh and treated catalyst compositions conducted in Example 10.
Figure 3B:
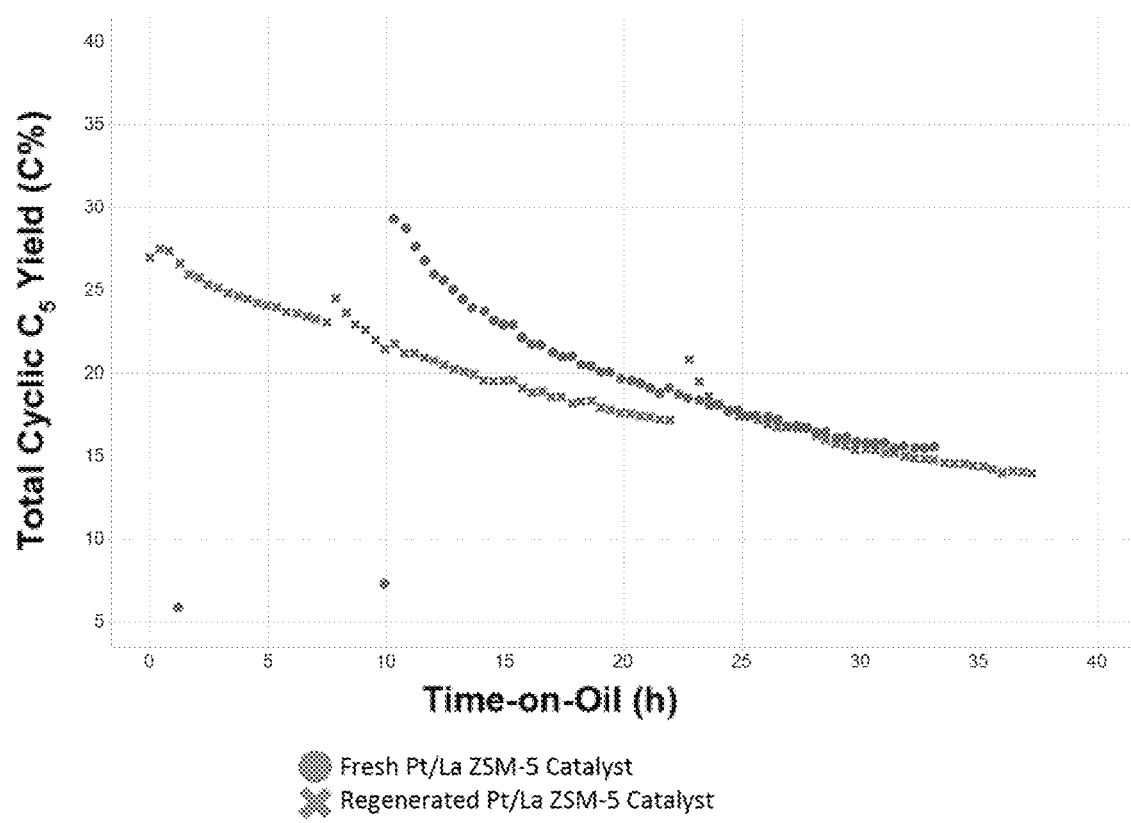

The performance test results and summarized in FIG. 3A and FIG. 3B. FIG. 3A shows the total cyclic $C_5$ yield for the fresh and treated Pt/Rh catalyst against time-on-oil, and FIG. 3B shows the total cyclic $C_5$ yield for the fresh and treated Pt/La catalyst against time-on-oil, with the exception that data collection for the fresh Pt/La catalyst did not being until t=10 hours-on-oil. As can be seen from FIG. 3A and FIG. 3B, both the Pt/Rh and Pt/La catalyst compositions subjected to the oxychlorination and chlorine stripping procedure demonstrated cyclization activity near that of the fresh catalyst. These data indicate that oxychlorination followed by chlorine stripping is a suitable regeneration method for these materials.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. For example, the compositions described herein may be free of any component, or composition not expressly recited or disclosed herein. Any method may lack any step not recited or disclosed herein. Likewise, the term "comprising" is considered synonymous with the term "including." And whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process for regenerating a deactivated catalyst comprising at least one Group 10 metal and a microporous crystalline aluminosilicate having a molar ratio of Group 10 metal to Al of greater than or equal to about 0.007:1 in a regeneration zone, wherein the microporous crystalline aluminosilicate is selected from the group consisting of ZSM-5, ZSM-11, ZSM-22, ZSM-23, ZSM-35, ZSM-48, ZSM-50, ZSM-57, ZSM-58, an MCM-22 family material, and mixtures or combinations thereof; the process comprising the steps of:
- a) supplying a first gaseous stream comprising a chlorine source and an oxygen source to the regeneration zone;
- b) contacting the catalyst with the first gaseous stream under conditions effective for dispersing at least a portion of the at least one Group 10 metal on the surface of the catalyst and for producing a first Group 10 metal chlorohydrate;
- c) withdrawing at least a portion of the first gaseous stream from the regeneration zone to form a first effluent;
- d) supplying a second gaseous stream comprising an oxygen source, and optionally a chlorine source, to the regeneration zone;
- e) contacting the catalyst produced in step b) with the second gaseous stream under conditions effective for increasing the O/Cl ratio of the first Group 10 metal chlorohydrate to produce a second Group 10 metal chlorohydrate;
- f) withdrawing at least a portion of the gaseous streams present in the regeneration zone from the regeneration zone to form a second effluent; and
- g) optionally, reducing at least a portion of the second Group 10 metal chlorohydrate to obtain a regenerated catalyst.

2. The process of claim 1, wherein the chlorine source in the first gaseous stream and/or the second gaseous stream is a member selected from the group consisting of HCl, $Cl_2$, chlorinated hydrocarbons, and mixtures or combinations thereof.

3. The process of claim 1, wherein the contacting of step b) is performed under conditions comprising a pressure of up to about 100 bar, $\log(PCl_2)$ in the first effluent ranging from about −15.0 to about 5.0, $\log(PO_2)$ in the first effluent ranging from about −5.0 to about 2.0, and a contacting temperature ranging from about 400° C. to about 750° C.

4. The process of claim 1, wherein the second gaseous stream has the same composition as the first gaseous stream.

5. The process of claim 4, wherein the contacting of step e) is performed under the same conditions as the conditions of step b), with the exception that the contacting temperature of step e) ranges from about 20° C. to about 200° C. below the contacting temperature of step b).

6. The process of claim 1, wherein the first Group 10 metal chlorohydrate is represented by Formula I:

$$[M(OH)_xCl_y]^a \qquad \text{Formula I}$$

wherein M is a Group 10 metal, x is an integer ranging from 0 to 4, y is an integer ranging from 2 to 6, wherein the sum of x and y ranges from 4 to 6, and wherein a is an integer ranging from −2 to 0.

7. The process of claim 6, wherein the second Group 10 metal chlorohydrate is represented by Formula II:

$$[M(OH)_zCl_w]^b \qquad \text{Formula II}$$

wherein M is a Group 10 metal, z is an integer ranging from 2 to 5, w is an integer ranging from 1 to 4, wherein the sum of z and w ranges from 4 to 6, and wherein b is an integer ranging from −2 to 0, wherein z>x and wherein w<y.

8. The process of claim 1, wherein the first and/or second gaseous stream further comprises from about 500 vppm to about 20,000 vppm $H_2O$ based on the total volume of the gaseous stream.

9. The process of claim 1, further comprising h) recycling at least a portion of the first effluent to step a) and/or recycling at least a portion of the second effluent to step d).

10. The process of claim 9, wherein the first gaseous stream comprises a mixture of $O_2$, HCl, $Cl_2$, and $H_2O$ components, and wherein each of the $O_2$, HCl, $Cl_2$, and $H_2O$ components is supplied to the regeneration zone within about 20% of the chemical equilibrium concentration of the component.

11. The process of claim 10, further comprising i) reducing the concentration of $H_2O$ and/or HCl in the first effluent prior to recycling.

12. The process of claim 10, further comprising j) increasing the concentration of $O_2$ and/or $Cl_2$ in the first effluent prior to recycling.

13. The process of claim 1, wherein the Group 10 metal is platinum.

14. The process of claim 1, wherein the catalyst further comprises one or more additional metals selected from the group consisting of Group 1 metals, Group 2 metals, Group 8 metals, Group 9 metals, Group 11 metals, rare earth metals, and mixtures or combinations thereof.

15. The process of claim 1, wherein the microporous crystalline aluminosilicate comprises ZSM-5.

16. The process of claim 1, wherein the catalyst further comprises a binder comprising one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof.

17. The process of claim 1, further comprising:
- a-0) contacting the catalyst with a third gaseous stream under conditions effective to remove at least a portion of coke from the catalyst, wherein the third gaseous stream comprises at least one of:
  - i. an oxygen source, and optionally a chlorine source; and/or
  - ii. hydrogen.

18. The process of claim 1, wherein step g) comprises contacting the catalyst with a fourth gaseous stream comprising about 10 vol % to about 100 vol % hydrogen based on the total volume of the fourth gaseous stream at a temperature ranging from about 200° C. to about 650° C.

19. The process of claim 18, wherein the fourth gaseous stream comprises CO, $CO_2$, $H_2O$, and/or hydrocarbon, and wherein the concentration of each of CO, $CO_2$, $H_2O$, and/or hydrocarbon in the fourth gaseous stream is less than 100 vppm based on the total volume of the fourth gaseous stream.

20. The process of claim 1, further comprising k) contacting the catalyst with a fifth gaseous stream comprising a sulfur source under conditions effective to deposit sulfur on the catalyst at a concentration ranging from about 10 to about 1,000 ppmw based on the total weight of the catalyst.

21. A process for regenerating a deactivated catalyst comprising at least one Group 10 metal and a microporous crystalline aluminosilicate having a molar ratio of Group 10 metal to Al of greater than or equal to about 0.007:1 in a regeneration zone, the process comprising the steps of:
- a) supplying a first gaseous stream comprising a chlorine source and an oxygen source to the regeneration zone;
- b) contacting the catalyst with the first gaseous stream under conditions effective for dispersing at least a portion of the at least one Group 10 metal on the surface of the catalyst and for producing a first Group 10 metal chlorohydrate;

c) withdrawing at least a portion of the first gaseous stream from the regeneration zone to form a first effluent;
d) supplying a second gaseous stream comprising an oxygen source, and optionally a chlorine source, to the regeneration zone;
e) contacting the catalyst produced in step b) with the second gaseous stream under conditions effective for increasing the O/Cl ratio of the first Group 10 metal chlorohydrate to produce a second Group 10 metal chlorohydrate;
f) withdrawing at least a portion of the gaseous streams present in the regeneration zone from the regeneration zone to form a second effluent; and
g) contacting the catalyst with a fourth gaseous stream comprising about 10 vol % to about 100 vol % hydrogen based on the total volume of the fourth gaseous stream at a temperature ranging from about 200° C. to about 650° C.

22. The process of claim 21, wherein the microporous crystalline aluminosilicate is selected from the group consisting of ZSM-5, ZSM-11, ZSM-22, ZSM-23, ZSM-35, ZSM-48, ZSM-50, ZSM-57, ZSM-58, an MCM-22 family material, and mixtures or combinations thereof.

* * * * *